US006358926B2

(12) United States Patent
Donovan

(10) Patent No.: US 6,358,926 B2
(45) Date of Patent: *Mar. 19, 2002

(54) NEUROTOXIN THERAPY FOR INNER EAR DISORDERS

(75) Inventor: Stephen Donovan, Capistrano Beach, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/864,447

(22) Filed: May 24, 2001

Related U.S. Application Data

(63) Continuation of application No. 09/418,192, filed on Oct. 13, 1999, now Pat. No. 6,265,379.

(51) Int. Cl.[7] .............................................. A61K 38/00

(52) U.S. Cl. ..................................................... 514/14

(58) Field of Search ......................... 424/236.1, 239.1; 514/14

(56) References Cited

U.S. PATENT DOCUMENTS

| | | | | |
|---|---|---|---|---|
| 5,714,468 A | * | 2/1998 | Binder | ........................ 514/14 |
| 5,766,605 A | | 6/1998 | Sanders et al. | |
| 6,265,379 B1 | * | 7/2001 | Donovan | ..................... 514/14 |

FOREIGN PATENT DOCUMENTS

| | | |
|---|---|---|
| WO | 94/21300 | 9/1994 |

OTHER PUBLICATIONS

G.E. Bryce, "Botulinum toxin treatment of essential palatal myoclonus tinnitus," Journal of Otolaryngology, vol. 27, No. 4, Aug. 1998, pp. 213–221.
S.M. Varney, et al., "Palatal myoclonus: Treatment with Clostridium botulinum toxin injection," Otolaryngology—Head and Neck Surgery, vol. 114, No. 2, 1996, pp. 317–320.
L. Badia, et al., "Management of middle ear myoclonus," Journal of Laryngology and Otology, vol. 108, No. 5, 1994, pp. 380–382.
Atkinson, M.; Tinnitus Aurium—Some Considerations Concernings Its Origin and Treatment; *Archives of Otolaryngol*, (1985); 45:68–76.
Badia, L., et al.; Management of Middle Ear Myoclonus; *The Journal of Laryngology and Otology*; May 1994; vol. 108; 380–382.
Bento, R. F., et al.; Continuous, High–Frequency Objective Tinnitus Caused by Middle Ear Myoclonus; *Ear, Nose & Throat Journal*, (Oct. 1998); 814–818.
Bottrill, I.D., et al.; Endoscope–Assisted Ear Surgery; *The American Journal of Otology*; vol. 16, No. 2; Mar. 1995; 158–163.
Bryce, G.E., et al.; Botulinum Toxin Treatment of Essential Palatal Myoclonus Tinnitus; *The Journal of Otolaryngology*; vol. 27, No. 4 (1998): 213–221.

Chaudhuri, K.R., et al.; The Moving Ear Syndrome: A Focal Dyskinesia; *Journal of Neurology, Neurosurgery, and Psychiatry* (Letters to the Editor); 1996; 60:106–110.
Coles, R. R. A., et al.; Some Varieties of Objective Tinnitus; *British Journal of Audiology*; (1975);9:1–6.
Deuschl, G., et al.; Ear Click in Palatal Tremor: Its Origin and Treatment with Botulinum Toxin; *Neurology*; (Oct. 1991); vol. 41:1677–1679.
Glanville, J. D., et al.; A Family with High–Tonal Objective Tinnitus; *The Journal of Laryngology and Otology*. (Jan. 1971); 1–10.
Hallett, M.; One Man's Poison—Clinical Applications of Botulinum Toxin; *The New England Journal of Medicine*; Jul. 8, 1999; 118–120.
Hentzer, E.; Objective Tinnitus of the Vascular Type—A Follow–up Study; *Acta otolaryngologica*; (1968); 66:273–281.
Huizing, E.H., et al.; An Unusual Type of Tinnitus; *Arch Otolaryngol*; (Aug. 1973); 98:134–136.
Karhuketo, T.S., et al.; Endoscopy of the Middle Ear Structures; *Acta Otolaryngol (Stockh)*; (1997); Suppl 529:34–39.
Klochoff, I.; Impedance Fluctuation and a "Tensor Tympani Syndrome"; *Acoustic Impedance Measurement*; Proc. 4th Intl Symp; (1981); 69–76.
Marchiando, A., et al.; Tinnitus Due to Idiopathic Stapedial Muscle Spasm; *Ear, Nose & Throat Journal*; (Jan. 1983); 62:8–13.
Piji, S.; Audiologic Findings in Botulism Poisoning; *Ear and Hearing*; vol. 12, No. 4, 1991; 281–286.
Pulec, J. L., et al.; Tinnitus: Diagnosis and Treatment; *Ann Otol*; (1978); 87–821–833.
Ragona, R.M., et al.; Management of Parotid Sialocele with Botulinum Toxin; *Laryngoscope*; vol. 109; Aug. 1999; 1344–1346.
Silverstein, H., et al.; Direct Round Window Membrane Application of Gentamicin in the Treatment of Meniere's Disease; *Otolaryngology—Head and Neck Surgery*; May 1999; vol. 120; No. 5; 649–655.
Silverstein, H., et al.; Inner Ear Perfusion and the Role of Round Window Patency; *The American Journal of Otology*; 1997; 18:586–589.
Silverstein, H., et al., Laser–Assisted Otoendoscopy; *ENT–Ear, Nose & Throat Journal*; Sep. 1997; 674–678.
Sismanis, A., et al.; A Practical Device for Detection and Recording of Objective Tinnitus; *Otolaryngology—Head and Neck Surgery*; (Apr. 1994); 110:459–462.
Swanson, P. D., et al.; Myoclonus—A Report of 67 Cases and Review of the Literature; *Medicine*; (1962); 41:339–356.

(List continued on next page.)

(57) ABSTRACT

Methods for treating otic disorders by local administration of a neurotoxin. A *botulinum* toxin can be administered to myoclonic middle ear muscles and to inner ear efferent and/or afferent nerves to alleviate otic disorders such as tinnitus, cochlear nerve dysfunction and Meniere's disease.

19 Claims, No Drawings

OTHER PUBLICATIONS

Tschabitscher, M., et al.; Two–Port Endoscopy of the Middle Ear; *Arch Otolaryngol Head Neck Surg*; (Apr. 1999); 125;433–437.

Vernon, J.A.; *Tinnitus—Treatment and Relief*; Allyn and Bacon; 1998. (Book—title pages only enclosed).

Watanabe, I., et al.; Tinnitus due to Abnormal Contraction of Stapedial Muscle; *ORL*; (1974); 36:217–226.

\* cited by examiner

*Primary Examiner*—Frederick Krass
*Assistant Examiner*—Donna Jague
(74) *Attorney, Agent, or Firm*—Martin A. Voet; Robert J. Baran; Carlos A. Fisher

NEUROTOXIN THERAPY FOR INNER EAR DISORDERS

CROSS REFERENCE

This application is a continuation of Ser. No. 09/418,192, now U.S. Pat. No. 6,265,379 B1, filed Oct. 13, 1999.

BACKGROUND

The present invention relates to methods for treating otic disorders. In particular the present invention relates to methods for treating otic disorders by local administration of a neurotoxin to a human ear.

The human ear can be divided into an outer ear, a middle ear and an inner ear. The outer ear comprises the auricle (commonly referred to as the ear) and the external acoustic meatus (the auditory canal). The tympanic membrane (commonly called the eardrum) separates the auditory canal from the middle ear (the tympanic cavity). Three small, mobile bones, the incus, malleus and stapes make up an ossicular system which conducts sound through the middle ear to the cochlea. The handle of the malleus is attached to the center of the tympanic membrane. At its opposite end, the malleus is bound to the incus by ligaments, so that movement of the malleus causes the incus to also move. The opposite end of the incus articulates with the stem of the stapes. The faceplate of the stapes rests against the membranous labyrinth in the opening of the oval window, where sound waves are conducted into the inner ear. In the cochlea the sound waves are transduced into coded patterns of impulses transmitted along the afferent cochlear fibers of the vestibulocochlear nerve for analysis in the central auditory pathways of the brain.

The air filled tympanic cavity contains various muscles including the tensor tympani and stapedius muscles. The tensor tympani is a long slender muscle which occupies the bony canal above the osseous pharyngotympanic tube, from which it is separated by a thin bony septum. The tensor tympani muscle receives both motor and proprioceptive innervation. A motor branch derived from the nerve to the medial pterygoid (mandibular division of the V, parasympathetic, trigeminal nerve) passes through the otic (a peripheral, parasympathetic cholinergic) ganglion to the tensor tympani. The stapedius muscle extends from the wall of a conical cavity in the pyramidal eminence, located on the posterior wall of the tympanic cavity. The stapedius is innervated by a branch of the (VII, parasympathetic) facial nerve.

Middle ear structures can be examined endoscopically, as set forth by Karhuketo et al., *Endoscopy of the Middle Ear Structures*, Acta Otolaryngol (Stockh) 1997; Suppl 529:34–39, the contents of which publication are incorporated herein by reference. There are many diseases of the ear including otis media. Otis media is an inflammation of the middle ear, commonly due to infection, and treatable by antibiotics. Alternate treatments for otis media include analgesics, antipyretics and myringotomy.

Loud noise can cause a muscular reflex to arise which attenuates the effect of excessive loud sound upon the middle and inner ear. Thus, the tensor tympani muscle can contract and pull the handle of the malleus inward while the stapedius muscle contracts and pulls the stapes outward. These two forces oppose each other and result in a high degree of rigidity developing in the ossicular system, thereby greatly reducing (by about 30–40 decibels) conduction of low frequency sounds by the ossicular system. This attenuation reflex can protect the cochlea against the damaging vibrations which would otherwise be induced by loud noise and may also act, mask out low frequency sound in a loud environment, and decrease a person's hearing sensitivity to his own voice.

The inner ear comprises the osseous labyrinth and the contained membranous labyrinth. The osseous labyrinth has three regions, the vestibule, the semicircular canals and the cochlea. The membranous labyrinth can be divided into the vestibular apparatus and the cochlear duct. In the walls of the membranous labyrinth within the vestibular apparatus are five distinct area of specialized sensory epithelium to which the terminal fibers of the vestibular nerve are distributed. Hair cells (epitheliocyti pilosi) in the cochlea are the sensory transducers which collectively detect the amplitude and frequency of sound waves entering the cochlea. The efferent innervation of at least the outer hair cells is cholinergic. Afferent innervation of the hair cells is complex and may involve release of one or more neurotransmitters, including glutamate.

Tinnitus

Tinnitus is a perception of sound which originates in the head. It has been estimated that 36 million Americans have some form of tinnitus and that one third of these have severe tinnitus, that is 12 million Americans hear tinnitus all he time (Vernon. J. A., *Tinnitus Treatment and Relief*, Allyn & Bacon (1998)). In objective tinnitus, the sound is audible, can be heard upon examination of the patient, and frequently corresponds to respiration. In the more frequent subjective tinnitus the sound cannot be heard by someone other than the patient. Tinnitus can be due to myoclonus of the palatal, tensor tympani and/or stapedius muscles.

Myoclonus is a sudden, involuntary movement caused by a muscle contraction or muscle inhibition and can be classified as physiologic, essential, epileptic and symptomatic myoclonus. Palatal myoclonus is characterized by involuntary movements of the soft palate and pharynx. The rhythmic involvement of the eustachian tube can result in the production of audible clicking sound synchronous with the palatal myoclonus. In palatal myoclonus the patient hears an irregular clicking sound coming form one or both ears. The condition is caused by myoclonic contractions in tensor or levator palati muscles or both. The injection of *botulinum* toxin into the soft palate has been effective to treat palatal myoclonus.

Myoclonus of the middle ear is characterized by abnormal repetitive muscle contractions in the tympanic cavity and can result in subjective or objective tinnitus. Permanent relief has been obtained by sectioning or by lysis of the tendons of the stapedius and tensor tympani muscles.

Inner ear tinnitus has been treated by section of the auditory nerve. Animal studies have shown that drugs, such a aspirin, which are known to cause tinnitus, do so with an increase in activity of the auditory nerve. It has therefore been speculated that a decrease in the endocochlear potential by down regulation of the auditory nerve may alleviate tinnitus.

A particular form of inner ear tinnitus is cochlear synaptic (cochlear nerve dysfunction) tinnitus which is due to functional disturbances of the synapse between cochlear hair cells and afferent dendrites of the auditory nerve. The neurotransmitter at the afferent cochlear synapse is glutamate. The majority of patients with cochlear synaptic tinnitus intravenously infused with the glutamate antagonists glutamic acid diethyl ester and caroverine have noted a tinnitus reduction. Drug therapy for inner ear tinnitus has included benzodiazepine tranquilizers such as valium and Xanas (alprazolam), a powerful anxiolytic drug which has strong addictive properties and can cause personality changes. The local anesthetic lidocaine has been proven to relive tinnitus. Unfortunately, because of serious toxicity, lidocaine must be given intravenously and it's effect lasts for only about 5–30 minutes.

Tensor tympani syndrome is a condition in which increased tension in the tensor tympani muscle produces a fluttering low frequency sound in the ear. In many cases the sound is also felt, as if there is a fluttering insect in the bottom of the ear canal. This is caused by the tympanic membrane being rapidly moved by the fibrillation of this middle ear muscle. Therapy includes section of the tendon of the tensor tympani muscle behind the neck of the malleus.

Tinnitus resulting from Meniere's disease can be treated by sectioning the vestibular nerve. Auditory nerve section has been used as a means of treating intractable tinnitus, often with the condition worsening because the tinnitus was not due to a cochlea disorder, prior to irreversible ablative surgery, after which no residual hearing will remain in the ear operated upon.

Botulinum Toxin

The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of *botulinum* toxin (purified neurotoxin complex) type A[1] is a $LD_{50}$ in mice. One unit (U) of *botulinum* toxin is defined as the $LD_{50}$ upon intraperitoneal injection into female Swiss Webster mice weighing 18–20 grams each. Seven immunologically distinct *botulinum* neurotoxins have been characterized, these being respectively *botulinum* neurotoxin serotypes A, B, $C_1$, D, E, F and G each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times the primate $LD_{50}$ for *botulinum* toxin type A. *Botulinum* toxin apparently binds with high affinity to cholinergic motor neurons, is translocated into the neuron and blocks the release of acetylcholine.

*Botulinum* toxins have been used in clinical settings for the treatment of neuromuscular disorders characterized by hyperactive skeletal muscles. *Botulinum* toxin type A has been approved by the U.S. Food and Drug Administration for the treatment of blepharospasm, strabismus and hemifacial spasm. Non type A *botulinum* toxin serotypes apparently have a lower potency and/or a shorter duration of activity as compared to *botulinum* toxin type A. Clinical effects of peripheral intramuscular *botulinum* toxin type A are usually seen within one week of injection. The typical duration of symptomatic relief from a single intramuscular injection of *botulinum* toxin type A averages about three months.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, *botulinum* toxin type $C_1$ has been shown to cleave both syntaxin and SNAP-25. These differences in mechanism of action may affect the relative potency and/or duration of action of the various *botulinum* toxin serotypes.

The molecular weight of the *botulinum* toxin protein molecule, for all seven of the known *botulinum* toxin serotypes, is about 150 kD. Interestingly, the *botulinum* toxins are released by Clostridial bacterium as complexes comprising the 150 kD *botulinum* toxin protein molecule along with associated non-toxin proteins. Thus, the *botulinum* toxin type A complex can be produced by Clostridial bacterium as 900 kD, 500 kD and 300 kD forms. *Botulinum* toxin types B and $C_1$ is apparently produced as only a 500 kD complex. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine, CGRP and glutamate.

*Botulinum* toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

It has been reported that *botulinum* toxin type A has been used in clinical settings as follows:

(1) about 75–125 units of BOTOX® per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

What is needed therefore is an effective, non-surgical ablation, non-radiotherapy therapeutic method for treating otic disorders, including middle ear tinnitus, inner ear tinnitus and myoclonic ear muscle tinnitus.

SUMMARY

The present invention meets this need and provides an effective, non-surgical ablation, non-radiotherapy therapeutic method for treating otic disorders, including middle ear tinnitus, inner ear tinnitus, and myoclonic ear muscle tinnitus.

A method within the scope of the present invention for treating an otic disorder has the step of local administration of a neurotoxin to an ear of a patient. By local administration it is meant that the neurotoxin is administered, as by injection, directly to, in, or to the vicinity of, the region of the ear to be treated. Preferably, the neurotoxin is injection into the middle or inner ear since otic disorders predominate in these areas.

The neurotoxin can be locally administered in an amount of between about $10^{-3}$ U/kg of patient weight and about 35 U/kg of patient weight. Preferably, the neurotoxin is locally administered in an amount of between about $10^{-2}$ U/kg and about 25 U/kg. More preferably, the neurotoxin is administered in an amount of between about $10^{-1}$ U/kg and about 15 U/kg. In a particularly preferred method within the scope of the present invention, the neurotoxin is locally administered in an amount of between about 1 U/kg and about 10 U/kg. In a clinical setting it can be advantageous to inject from 1 U to 10 U of a neurotoxin, such as *botulinum* toxin type A, into a middle or inner ear structure to effectively treat an otic disorder.

A suitable neurotoxin for use in the practice of the present invention can be made by a Clostridial bacterium, such as *Clostridium botulinum, Clostridium butyricum* or *Clostridium beratti*. The neurotoxin use can be a modified neurotoxin, that is a neurotoxin has had at least one of its amino acids deleted, modified or replaced, as compared to a native neurotoxin. Additionally, the neurotoxin can be recombinantly made produced neurotoxin or a derivative or fragment of a recombinant made neurotoxin. The neurotoxin can be a *botulinum* toxin, such as one of the *botulinum* toxin serotypes A, B, C1, D, E, F or G. A preferred *botulinum* toxin to use in the practice of the present invention is *botulinum* toxin type A.

The otic disorder treated can be a hearing impairment, tinnitus, vertigo, dizziness and/or headache and the neurotoxin can is locally administered to the outer ear, the middle ear or the inner ear. A method for treating tinnitus within the scope of the present invention can comprise the step of local administration of a therapeutic amount of a *botulinum* toxin to the middle or inner ear of a human patient to thereby substantially alleviating the tinnitus. The tinnitus can be treated by local administration of a *botulinum* toxin to a myoclonic middle ear muscle, such as a myoclonic stapedius or tenor tympani muscle.

A detailed method within the scope of the present invention for in vivo treatment of a non-infectious disorder of the middle or inner ear of a human patient can comprise the step of local administration to the middle ear or inner ear of the human patient of a therapeutically effective amount of a *botulinum* toxin, thereby causing or resulting in an in vivo attenuation of the non-infectious middle or inner ear disorder of the human patient. A further method within the scope of the present invention is a method for improving patient function, the method comprising the step of administering a neurotoxin to an ear of a human patient, thereby improving patient function as determined by improvement in one or more of the factors of reduced pain, reduced time spent in bed, improve hearing, increased ambulation, healthier attitude and a more varied lifestyle.

Notably, the disclosed methods can be used to treat inner ear otic disorders such as Meniere's disease and cochlear nerve dysfunction.

DESCRIPTION

The present invention is based upon the discovery that otic disorders, such as some forms of tinnitus, can be treated by local administration of a neurotoxin, such as a *botulinum* toxin. By local administration it is meant that the neurotoxin is administered directly to, in, or to the vicinity of, the ear or ear region to be treated. Local administration includes otic intramuscular, intratympanic cavity and intracochlear injection routes of administration for the neurotoxin. Peripheral (i.e. limb) muscle intramuscular, intrasphincter (i.e. in the GI tract), oral, and subcutaneous drug administration routes are unsuited for the practice of the present invention and are excluded from its scope.

The present invention is not intended for the treatment of an infectious otic disorder, such as otis media, because the neurotoxins administered do not exhibit an antibiotic effect. It is known to inject or infuse antibiotics into the tympanic cavity, as set forth, for example in Otolaryngol Head Neck Surg. 1999 May;120(5):649–55, and Am J Otol 1997 Sep;18 (5):586–9, the contents of which two publications are incorporated herein by reference in their entireties.

I have discovered that a particular neurotoxin, botulinum toxin, can be used with dramatic ameliorative effect to treat tinnitus thereby significantly superseding current surgical and radiotherapy therapeutic methods used to treat tinnitus. Significantly, a single administration of the botulinum toxin can substantially also reduce the headache, vertigo and anxiety symptoms which can accompany tinnitus.

The route of administration and amount of botulinum toxin administered can vary widely according to the particular otic disorder being treated and various patient variables including size, weight, age, disease severity and responsiveness to therapy. Additional factors affecting determination of an appropriate route for administration of a neurotoxin according to the present disclosed invention for treating an otic disorder can include solubility characteristics of the neurotoxin toxin chosen as well as the amount of the neurotoxin to be administered. For example, the extent of otic muscle or nerve area influenced is believed to be proportional to the volume of neurotoxin injected, while the quantity of the denervation is, for most dose ranges, believed to be proportional to the concentration of neurotoxin injected. The specific dosage appropriate for administration is readily determined by one of ordinary skill in the art according to the factor discussed above. The dosage can depend upon the size of the muscle to be denervated, the degree of weakness required and the commercial preparation of the toxin. Additionally, the estimates for appropriate dosages in humans can be extrapolated from determinations of the amounts of botulinum required for effective denervation of other non-otic muscles.

Methods for determining the appropriate route of administration and dosage are generally determined on a case by case basis by the attending physician. Such determinations are routine to one of ordinary skill in the art (see for example, Harrison's Principles of Internal Medicine (1997), edited by Anthony Fauci et al., 14$^{th}$ edition, published by McGraw Hill). For example, to treat tinnitus due to a myoclonic middle ear muscles, a solution of botulinum toxin type A complex can be endoscopically administered intramuscular directly to the hyperactive muscle, thereby substantially avoiding entry of the toxin into the systemic circulation.

Preferably, a neurotoxin used to practice a method within the scope of the present invention is a botulinum toxin, such as one of the serotype A, B, $C_1$, D, E, F or G botulinum toxins. Preferably, the botulinum toxin used is botulinum toxin type A, because of its high potency in humans, ready availability, and known use for the treatment of skeletal and smooth muscle disorders when locally administered by intramuscular injection.

Careful placement of the injection needle and a low volume of neurotoxin used prevents significant amounts of botulinum toxin from appearing systemically. The actual amount of U/kg of a botulinum toxin to be administered depends upon factors such as the extent (mass) of the otic tissue to be treated and the administration route chosen. A range for direct otic administration of a botulinum toxin, such as botulinum toxin type A, so as to achieve an alleviation of middle ear tinnitus, inner ear tinnitus in the patient treated is from about $10^{-3}$ U/kg to about 35 U/kg. Less than about $10^{-3}$ U/kg result in a relatively minor, though still observable, therapeutic results (i.e. alleviation of myoclonia), while more than about 35 U/kg can result in excessive peripheral muscle flaccidity and symptoms of toxin intoxication. A more preferred range for intrathecal administration of a botulinum toxin, such as botulinum toxin type A, so as to achieve a desired therapeutic effect in the patient treated is from about $10^{-2}$ U/kg to about 25 U/kg. Less than about $10^{-2}$ U/kg result in a low to moderate therapeutic results while more than about 25 U/kg can result in significant symptoms of peripheral muscle flaccidity. A most preferred range for direct administration of a botulinum toxin, such as botulinum toxin type A, so as to achieve a desired therapeutic effect in the patient treated is from about $10^{-2}$ U/kg to about 15 U/kg. More than about 15 U/kg can still result in some symptoms of muscle flaccidity.

The relatively same size and mass of the stapedius and tensor tympani muscles makes a range of from about 1 U to about 50 U (total units) suitable of a botulinum toxin, such as botulinum toxin type A, preferred for effective for long lasting and significant relief from the tinnitus due to specifically to myoclonic stapedius and tensor tympani muscles. A more preferred range for effective for long lasting and significant relief from the tinnitus due to specifically to myoclonic stapedius and tensor tympani muscles is from about 1 U to about 25 U (total units). All dosage amount set forth about are per injection. Most preferably, considering the small size of the stapedius and tensor tympani muscles, from about 1 U to about 10 U per injection (i.e. once every 2–6 months) of intramuscular botulinum toxin type A can be injected into each of these two middle ear muscles to thereby provide substantial relief from tinnitus.

The present invention includes within its scope the use of any neurotoxin which has a long duration therapeutic effect when locally applied to an otic region or structure of a patient. For example, neurotoxins made by any of the species of the toxin producing Clostridium bacteria, such as Clostridium botulinum, Clostridium butyricum, and Clostridium beratti can be used or adapted for use in the methods of the present invention. Additionally, all of the botulinum serotypes A, B, $C_1$, D, E, F and G can be advantageously used in the practice of the present invention, although type A is the most preferred serotype, as explained above. Practice of the present invention can provide a significant therapeutic effect, per injection, for 2–6 months or longer in humans.

The therapeutic relief provided by a single injection of botulinum toxin type A has been demonstrated to last at least as long as 27 months, and possibly permanently for some types of disorders depending upon the site and dosage injected, among other factors. Hence, it is within the scope of the present invention to provide long lasting therapeutic relief from an otic disorder by the methods disclosed herein.

It is the inventor's contention that a botulinum toxin can block the release of any vesicle mediated exocytosis from any neuronal cell type, as long as the light chain of the botulinum toxin is translocated into the intracellular medium. For example, the intracellular protein SNAP-25 is widely distributed in neuronal cells and *botulinum* toxin type A is an endopeptidase for which the specific substrate is SNAP-25. Thus, while cholinergic neurons have a high affinity acceptor for the *botulinum* and tetanus toxins (and are therefore more sensitive than other neurons and other cells to the inhibition of vesicle mediated exocytosis of secretory compounds), as the toxin concentration is raised, non-cholinergic sympathetic neurons can take up a *botulinum* toxin and show reduced exocytosis of neurotransmitters other than acetylcholine.

Hence, by practice of the present disclosed invention, non-cholinergic inner ear nerve fibers can be treated by use of an appropriately higher concentration of a *botulinum* toxin to bring about therapeutic inner ear denervation (i.e. effective treatment of inner ear tinnitus).

Furthermore, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone.

The present invention includes within its scope: (a) neurotoxin complex as well as pure neurotoxin obtained or processed by bacterial culturing, toxin extraction, concentration, preservation, freeze drying (or vacuum drying) and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, and includes neurotoxins with one or more attached or recombinantly fused neuronal targeting moieties.

*Botulinum* toxins for use according to the present invention can be stored in lyophilized or vacuum dried form in containers under vacuum pressure. Prior to lyophilization the *botulinum* toxin can be combined with pharmaceutically acceptable excipients, stabilizers and/or carriers, such as albumin. The lyophilized or vacuum dried material can be reconstituted with saline or water.

The present invention can be practiced by transtympanic injection of *botulinum* toxin to reduce activity and tone of transtympanic muscles and thereby treat tinnitus, dysacusis (which can be defined as abnormal acoustic sensations, such as murmurs, clicks, tickling sensations and sound distortions, as well as pain or discomfort in the ear due to exposure to sound), tension headache, and vertigo (dizziness and dysequilbrium).

Without wishing to be bound to any particular theory, the mechanism of *botulinum* toxin activity upon middle ear tinnitus is believed to be by exertion of an anticholinergic effect. Thus, the stapedius muscle is innervated by cholinergic motor neurons derived from the facial nerve, while the tensor tympani muscle is innervated cholinergic motor neurons branching from the trigeminal nerve through the otic ganglion. A possible similar mechanism of action of *botulinum* toxin to treat inner ear tinnitus can be postulated. Hair cell efferents are believed to be influenced by acetylcholine and hair cell afferents may release glutamate. I have discovered that tinnitus resulting from abnormal neuronal activity of, or influence upon, inner ear hair cells can be treated by suppressing exocytosis in inner ear nerve fibers of the indicated neurotransmitters. Exocytosis is suppressed by local administration of a neurotoxin by the methods set forth herein.

A significant and important benefit of the disclosed invention is that it supercedes and renders unnecessary much highly invasive surgery. Thus, endoscopic and EMG recording, as opposed to open (i.e. craniotomy and dural incisions) surgical means (as opposed to the nominal invasive nature of a transtympanic approach) are used to access and treat a middle ear muscle (treatment of middle ear tinnitus) or the cochlea (treatment of inner ear tinnitus).

Endoscopic assisted (including laser assisted endoscopy to make an incision in the tympanic membrane) injection of a *botulinum* toxin to a middle or inner ear structure of a patient to treat an otic disorder according to the present invention can be carried out by application of or by facile adaptation of known endoscopic procedures, as set forth for example in Amer J. Otology 16 (2); 158–163 (March 1995), and Ear Nose Throat J. 76(9) 674–678 (September 1997), the contents of which two publications are incorporated herein by reference in their entireties.

Besides endoscopic assisted local administration of a neurotoxin to treat an otic disorder, the present methods can be practiced by injection through the tympanic membrane using a fine (EMG recording) needle, through use of an indwelling catheter placed through a myringotomy incision, and injection or infusion through the Eustachian tube by means of a small tubal catheter. Additionally, a neurotoxin can be administered to the inner ear by placement of a gelfoam, or similar absorbent and adherent product, soaked with the neurotoxin against the round window membrane of the middle/inner ear or adjacent structure.

EXAMPLES

The following examples provide those of ordinary skill in the art with specific preferred methods within the scope of the present invention for carrying out the present invention and are not intended to limit the scope of what the inventor regard as his invention.

One or two port endoscopy of the middle ear can be carried out. Thus, anatomical structures can be visualized by transmeatal or transtympanic rigid scopes of different angles and by a flexible scope in the eustachian tube. Three endoscopic routes to the middle ear can be used, these being: (1) transmeatal after raising a tympanomeatal flap, (2) transtympanic through a tympanic incision, and (3) the non-invasive through the preformed channel of the eustachian tube.

Example 1
Endoscopic Examination of the Middle Ear

A transtympanic endoscope can be used to view the tympanic cavity. A flexible, steerable scope with an outside diameter of 0.8 mm (12,000 pixels; angle of view, 70°; total length, 650 mm; deflection angle, 90°; and length of deflectable part 25 mm) obtained from Micromed Co, Dornbirn, Austria can be used for transtubal endoscopy. The patient's head can be positioned in 30° lateral decubitus. The transtubal scope can be introduced through a tubal catheter placed at the pharyngeal orifice of the eustachian tube under endoscopic guidance (rigid 70° scope) through the contralateral nasal airway. After removing the rigid scope, the flexible steerable scope can be advanced into the middle ear through the tubal catheter. Successful advancement of the scope to the middle ear requires an adequate width of the tubal isthmus (mean, 1.0 mm wide and 2 mm high).

Transmeatal or transtympanic endoscopy can be performed using a rigid scope. Depending on the approach chosen, the outside diameter of the scope can be either 2.3 or 1.9 mm, with angles of 0°, 30°, or 70° (Karl Storz, Tuttlingen, and Aesculap). For the transmeatal approach, the tympanic cavity can be opened by endoscopically raising a tympanomeatal flap so that the scope can enter the posterior part of the cavity below the incudostapedial joint. For the transtympanic approach, radial incisions can be made in the tympanic membrane either between the posterosuperior and the posteroinferior quadrant or in the anteroinferior quadrant, depending on the region of interest. Images can be recorded on a digital image recording device from S-VHS video sources (Digi-Still Unit and S-VHS Video Recorder; Sony, Vienna, Austria).

The field of view available depends on the angle of the scope (0°, 30°, or 70°). The 0° scopes can provide visualization only of the long process of the incus and the medial wall (labyrinthine wall). The 30° scopes can afford a larger view in all directions. The field of view can extend to the facial canal with the scope directed upward, to the round window niche with the scope directed downward, to the tympanic sinus with the scope directed posteriorly, and to the cochleariform process with the scope directed anteriorly. The 70° scope can offer an even wider view of the tympanic cavity. With these, the tympanic chord and the aditus ad antrum can be seen above, the hypotympanum below, the lateral sinus and facial recess posteriorly, and the tympanic orifice of the tube anteriorly.

With a transtubal endoscope, the isthmus can be successfully negotiated and passage aided by subtly maneuvering and turning the scope tip. Once the steerable scope has reached the protympanum, it can be advanced along 2 alternative routes: (1) above the tensor tendon into the epitympanum and then along the tegmen to the mastoid antrum; or (2) below the tensor tendon into the mesotympanum toward the incudostapedial joint and then either (a) medial to the incus and above the stapes into the aditus ad antrum or (b) lateral to the incus toward the tympanic chord or (c) below the stapes toward the lateral sinus. As the scope is advanced through the mesotympanum, it passes the entire tympanic membrane, which forms the lateral wall and can be inspected in its entire extension. Along the routes described, the flexible scope can be easily maneuvered past the ossicles without injuring them.

In each of the following examples, the specific amount of intramuscular BOTOX® administered depends upon a variety of factors to be weighed and considered within the discretion of the attending physician and in each of the examples insignificant amounts of *botulinum* toxin enter appear systemically with no significant side effects.

As well as endoscopic assistance, the intramuscular injection of a *botulinum* toxin is preferably carried out through an electromyrographic (EMG) recording needle so as to ensure insertion of the needle tip in muscle mass prior to injection of the toxin into the muscle. The EMG needle is electrically shielded except for its tip.

Example 2
Treatment of Objective Tinnitus

A 24 year old woman complains of a continuous high frequency sound in her right ear. The sound can be easily heard from a distance of 15 cm emanating from the patient's right exterior auditory canal, reliably matched by a 50 bD, 7 kHz external sound. She has had the tinnitus since childhood and sleep does not alleviate it. The tinnitus impairs her ability to concentrate, causes sleep disturbance and has a significant negative effect on her emotional well being. She occasionally experiences vertigo which she attributes to the extreme emotional distress caused by the tinnitus. No vascular etiology for the tinnitus can be discerned.

Transtympanic endoscopy is carried out, as set forth in Example 1, and from 1 unit to 50 units of a *botulinum* toxin A–G, such as BOTOX®, is injected directly into the stapedius and/or tensor tympani muscles of the patient's middle ear. Within 1–7 days the tinnitus is substantially alleviated and the symptoms do not return or return only after 2 to 4 months have elapsed after the single injection of the *botulinum* toxin.

Example 3
Treatment of Subjective Tinnitus

A 38 year old man complains of clicking tinnitus of 6 years duration. The quality of the sound is described as static. The tinnitus is precipitated by conversation and loud noises. It is exacerbated by prolonged sound exposure. There was no objective tinnitus. The patient undergoes right and left tympanotomy and injection of from 1 unit to 50 units of a *botulinum* toxin A–g, such as BOTOX®, is injected into the stapedius and/or tensor tympani muscles of the patient's middle ear. Within 1–7 days the tinnitus is substantially alleviated and the symptoms do not return or return only after 2 to 4 months have elapsed after the *botulinum* toxin injection, once in each middle ear.

Example 4
Treatment of Inner Ear Tinnitus

A 60 year old female complains bitterly of a loud, troublesome subjective tinnitus, vertigo and headache. Loud sounds disturb her excessively. Transtympanic injection of a muscle relaxant (Xylocaine) is ineffective, as is masking, weight reduction and biofeedback. No venous turbulence or eustachian tube etiology or can be determined. A diagnosis of cochlear nerve dysfunction (inner ear tinnitus) is made. As an alternative to labyrinthectomy or translabyrinthine VIII section, both of which are irreversible, from 1 unit to 50 units of a *botulinum* toxin A–G, such as BOTOX®, is injected into the vestibule in the vicinity of the cochleal nerve. Within 1–7 days the tinnitus is substantially alleviated and the symptoms do not return or return only after 2 to 6 months have elapsed after the *botulinum* toxin injection, once into or into the vicinity of the cocheal nerve.

Example 5
Treatment of Meniere's Disease

A 19 year old male presents with episodic rotational vertigo, hearing loss of the lower frequencies, tinnitus (a roaring, buzzing or ringing sound) in the right ear, and a sensation of fullness in the ear. Vertigo is, by far, the most troubling of the symptoms to the patient. The vertigo is accompanied by dysequilbrium (an off-balance sensation) and nausea. The vertigo can last for up to two hours per episodic occurrence. The patient states that insomnia frequently ensues after the vertigo.

A diagnosis of Meniere's disease is made. Rather than section the vestibular nerve, from 1 unit to 50 units of BOTOX® is injected into the cochlear or auditory nerve or into the vestibule in the vicinity of the cochleal nerve. Within 1–7 days after injection, all symptoms are substantially alleviated and the symptoms do not return or return 2 to 6 months subsequent to the single *botulinum* toxin injection.

Methods according to the invention disclosed herein has many advantages, including the following:

1. middle ear tinnitus can be substantially alleviated.
2. inner ear tinnitus can be substantially alleviated.
3. myoclonic middle ear muscles can be chemically, and reversibly denervated.

4. highly invasive surgical method as well as radiotherapy becomes unnecessary.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local otic administration methods wherein two or more neurotoxins, such as two or more *botulinum* toxins, are administered concurrently or consecutively. For example, *botulinum* toxin type A can be administered until a loss of clinical response or neutralizing antibodies develop, followed by administration of *botulinum* toxin type E. Alternately, a combination of any two or more of the *botulinum* serotypes A–G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a *botulinum* toxin, begins to exert its therapeutic effect.

My invention also includes within its scope the use of a neurotoxin, such as a *botulinum* toxin, in the preparation of a medicament for the treatment of an otic disorder, by local otic administration of the neurotoxin.

Accordingly, the spirit and scope of the following claims should not be limited to the descriptions of the preferred embodiments set forth above.

I claim:

1. A method for treating an otic disorder, the method comprising the step of local administration of a neurotoxin to an inner ear.

2. The method of claim 1, wherein the neurotoxin is administered in an amount of between about $10^{-3}$ U/kg and about 35 U/kg.

3. The method of claim 1, wherein the neurotoxin is administered in an amount of between about $10^{-2}$ U/kg and about 25 U/kg.

4. The method of claim 1, wherein the neurotoxin is administered in an amount of between about $10^{-1}$ U/kg and about 15 U/kg.

5. The method of claim 1, wherein the neurotoxin is administered in an amount of between about 1 U/kg and about 10 U/kg.

6. The method of claim 1, wherein the neurotoxin is made by a Clostridial bacterium.

7. The method of claim 1, wherein the neurotoxin is made by a bacterium selected from the group consisting of *Clostridium botulinum, Clostridium butyricum* and *Clostridium beratti.*

8. The method of claim 1, wherein the neurotoxin is a modified neurotoxin.

9. The method of claim 1, wherein the neurotoxin has at least one of its acids deleted, modified or replaced, as compared to a native neurotoxin.

10. The method of claim 1, wherein the neurotoxin is a recombinant produced neurotoxin or a derivative or fragment thereof.

11. The method of claim 1, wherein the otic disorder is a hearing impairment.

12. The method of claim 1, wherein the otic disorder is selected from the consisting of, tinnitus, vertigo, dizziness and headache.

13. The method of claim 1, wherein the otic disorder is tinnitus.

14. The method of claim 1, wherein the neurotoxin is locally administered by direct injection of the neurotoxin into the inner ear.

15. A method for treating tinnitus, the method comprising the step of local administration of a therapeutic amount of a neurotoxin to an inner ear of a human patient, thereby substantially alleviating the tinnitus.

16. A method for the in vivo treatment of a non-infectious disorder of an inner ear of a human patient, the method comprising the step of local administration to the inner ear of a human patient of a therapeutically effective amount of a neurotoxin, thereby causing an in vivo attenuation of a non-infectious disorder of the inner ear of the human patient.

17. The method of claim 16, wherein the non-infectious disorder of the inner ear is Meniere's disease.

18. The method of claim 16, wherein the non-infectious disorder of the inner ear is cochlear nerve dysfunction.

19. The method of claim 16, wherein the non-infectious disorder of the inner ear is tinnitus.

* * * * *